United States Patent [19]

Bamber et al.

[11] Patent Number: 5,659,035

[45] Date of Patent: Aug. 19, 1997

[54] SUBSTITUTED PHOSPHONIC ACIDS

[75] Inventors: Michael Bamber, Water Orton; Gary Woodward, Kidderminster, both of England

[73] Assignee: Albright & Wilson Limited, West Midlands, England

[21] Appl. No.: 351,752

[22] Filed: Dec. 8, 1994

[30] Foreign Application Priority Data

Dec. 8, 1993 [GB] United Kingdom ............. 9325113

[51] Int. Cl.[6] .................. C07F 9/564; C07F 9/572; C07F 9/58; C07F 9/28
[52] U.S. Cl. ................. 546/22; 546/23; 540/450; 540/542; 548/412
[58] Field of Search ............... 546/22, 23; 548/412; 540/450, 542

[56] References Cited

U.S. PATENT DOCUMENTS

| | | | |
|---|---|---|---|
| 3,734,914 | 5/1973 | Lorenz et al. | 546/23 |
| 3,941,772 | 3/1976 | Ploger et al. | 546/6 |
| 4,876,339 | 10/1989 | Blum et al. | 540/450 |

FOREIGN PATENT DOCUMENTS

| | | |
|---|---|---|
| 332068 | 9/1989 | European Pat. Off. . |
| 121644 | 8/1976 | Germany . |
| 2541981 | 3/1977 | Germany . |
| 4114586 | 11/1992 | Germany . |
| 1451865 | 10/1976 | United Kingdom . |

OTHER PUBLICATIONS

Chem. Abstracts, vol. 118(9)abst No. 80827t Mar. 1, 1993.
Chem. Abstracts, vol. 112(9)abst. No. 77540-Q Feb. 26, 1990.
Chem. Abstracts, vol. 87(7)abst. No. 53,437-a Aug. 15, 1977.

Primary Examiner—Alan L. Rotman
Attorney, Agent, or Firm—Frishauf, Holtz, Goodman, Langer & Chick, P.C.

[57] ABSTRACT

A method for the production of azacycloalkane-2,2-diphosphonic acids of general formula;

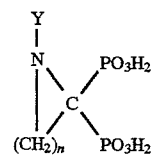

where n is a whole number of from 2 to 16, Y is H, an alkyl or alkenyl, a substituted alkyl, or an aryl, such that the group "Y" remains unchanged during the reaction, by reaction of a lactam with a phosphorus trihalide in the presence of phosphorous acid and/or water, in which the reaction mixture also includes an organic amine and/or or an organic amine salt, said reaction being followed by hydrolysis of the reaction mixture and purification of the reaction product to obtain the diphosphonic acid.

The method is exemplified by the preparation of azacycloheptane-2,2-diphosphonic acid, and azacyclononane-2,2-diphosphonic acid.

17 Claims, No Drawings

SUBSTITUTED PHOSPHONIC ACIDS

This invention relates to an improved method for the production of azacycloalkane-2,2-diphosphonic acids and to azacycloalkane-2,-2-diphosphonic acids obtained thereby. The present invention will be described herein with particular reference to azacycloheptane-2,2-diphosphonic acid and to azacyclononane-2,2-diphosphonic acid, although it is not to be construed as being limited thereto.

Throughout this description, the term "azacycloalkane-2,2-diphosphonic acid" denotes a compound of the general formula

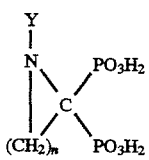

where n is a whole number of from 2 to 16 and Y is H, an alkyl or alkenyl, a substituted alkyl or an aryl group, such that the group "Y" remains unchanged during the reaction.

The preparation of azacycloheptane-2,2-diphosphonic acid (hereinafter AHP) has been described in U.S. Pat. No. 3,941,772, DEOS 2541981 and DEOS 3808074. The preparation of other azacycloalkane-2,2-diphosphonic acids, has been described in DEOS 4114586. All of these prior documents suggest that the use of toxic and/or expensive solvents (e.g., chlorobenzene, dioxane, and glycols) are essential in order to prevent the reaction mixture from becoming unstirrable and/or the reaction itself becoming unreproducible, and/or uneconomical due to the low yields of product obtained.

It has now been discovered that the addition of an organic amine and/or amine salt (e.g. an amine hydrochloride, amine hydrobromide or an amine salt of phosphorous acid) to a reaction mixture including a lactam, a phosphorus trihalide, phosphorous acid and/or water, followed by hydrolysis and subsequent purification of the product, leads to the production of the corresponding azacycloalkane-2,2-diphosphonic acid, in good yield, with the reaction mixture remaining stirrable throughout the reaction.

Accordingly, the present invention provides a method for the production of azacycloalkane-2,2-diphosphonic acids of general formula;

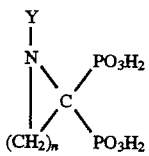

where n is a whole number of from 2 to 16 and Y is H, an alkyl or alkenyl, a substituted alkyl, or an aryl, such that the group "Y" remains unchanged during the reaction, by the reaction of a lactam with a phosphorus trihalide, in the presence of phosphorous acid and/or water, in which the reaction mixture also includes an organic amine and/or an organic amine salt, followed by hydrolysis of the reaction mixture and purification of the reaction product to obtain the diphosphonic acid.

The present invention also provides azacycloalkane-2,2-diphosphonic acids produced by the method described in the immediately-preceding paragraph.

The lactam may be, for example, caprolactam, whereby the acid produced is azacycloheptane-2,2-diphosphonic acid, or the lactam may be, for example, 2-azacyclononanone, whereby the acid produced is azacyclononane-2,2-diphosphonic acid.

The phosphorus trihalide is suitably phosphorus trichloride or phosphorus tribromide.

Preferably, the organic amine is a tertiary amine and the organic amine salt is a tertiary amine phosphorous acid salt, hydrochloride, or hydrobromide. Suitable amines and amine salts include triethylamine, tributylamine and their phosphorous acid salts hydrochlorides, or hydrobromides. The organic amine phosphorous acid salt may be formed in situ during the reaction.

The ratio of amine or amine salt to lactam in the reaction mixture is preferably about 1:1 molar, but may be in the range 0.1:1 to 4:1 molar, for example 0.1:1 to 2:1 molar, especially 0.5:1 to 2:1 molar.

Azacycloalkane-2,2-diphosphonic acids are known to exhibit excellent sequestering properties for polyvalent metal ions, especially di-and tri-valent metal ions, and AHP is known to be particularly suitable for use in toothpastes, toothpolishes and mouthwash formulations.

The present invention will be further illustrated by way of the following Examples:

EXAMPLE 1—Preparation of AHP

Into a stirred mixture of caprolactam (113 g, 1.0m), triethylamine hydrochloride (138 g, 1.0m) and water (60 g, 3.36m), was added phosphorus trichloride (292 g, 2.12m) over 40 minutes and at a temperature below 40° C. The reaction mixture was then heated over 120 minutes to 80° C. and held at this temperature for a further 120 minutes. During the total reaction time the reaction mixture was stirrable and no foaming took place. The mixture was hydrolysed at 80° C. with 400 ml of 20% hydrochloric acid then heated to reflux and held for 240 minutes. During this process the pale orange product precipitated and was isolated by filtration. For further purification, the crude product was suspended in water, adjusted to a pH value of 9 with sodium hydroxide solution, and the undissolved polymer product separated. After the acidification of the salt solution with concentrated hydrochloric acid to pH 1, the product was separated by filtration and vacuum dried.

Yield of AHP was 156 g, 60% of theoretical yield.

EXAMPLE 2—Preparation of AHP

Into a stirred mixture of caprolactam (57 g, 0.5m) tributylamine hydrochloride (89 g, 0.4m) and water (30 g, 1.65m), was added phosphorus trichloride (151 g, 1.1m) over 40 minutes and at a temperature below 40° C. The reaction mixture was then heated over 120 minutes to 90° C. and held at this temperature for a further 30 minutes. During the total reaction time the reaction mixture was stirrable and no foaming took place. The mixture was hydrolysed at 80° C. with 250 ml of 20% hydrochloric acid then heated to reflux and held for 180 minutes. During this process the pale orange product precipitated and was isolated by filtration. For further purification, the crude product was suspended in water, adjusted to a pH value of 9 with sodium hydroxide solution, and the undissolved polymer product separated. After the acidification of the salt solution with concentrated hydrochloric acid to pH 1, the product was separated by filtration and vacuum dried.

Yield of AHP was 53 g, 41% of theoretical yield.

EXAMPLE 3—Preparation of AHP

Into stirred and cooled triethylamine (51 g, 0.5m) was added 54 g of concentrated hydrochloric acid followed by caprolactam (57 g, 0.5m). To this solution was added phosphorus trichloride (151 g, 1.1m) over 40 minutes and at a temperature below 50° C. The reaction mixture was then heated over 120 minutes to 90° C. and held at this temperature for a further 30 minutes. During the total reaction time the reaction mixture was stirrable and no foaming took place. The mixture was hydrolysed at 60° C. with 200 g of water then heated to reflux and held for 60 minutes. During this process the pale orange product precipitated and was isolated by filtration. For further purification the crude product was suspended in water, adjusted to a pH value of 9 with sodium hydroxide solution, and the undissolved polymer product separated. After the acidification of the salt solution with concentrated hydrochloric acid to pH 1, the product was separated by filtration and vacuum dried.

Yield of AHP was 78 g, 60% of theoretical yield.

EXAMPLE 4—Preparation of AHP

Into stirred and cooled triethylamine (51 g, 0.5m) was added 54 g of concentrated hydrochloric acid followed by caprolactam (57 g, 0.5m). To this solution was added phosphorus trichloride (151 g, 1.1m) over 40 minutes and at a temperature below 50° C. The reaction mixture was then heated over 120 minutes to 110° C. and held at this temperature for a further 30 minutes. During the total reaction time the reaction mixture was stirrable and no foaming took place. The mixture was hydrolysed at 60° C. with 200 g of water then heated to reflux and held for 60 minutes. During this process the pale orange product precipitated and was isolated by filtration. For further purification, the crude product was suspended in water, adjusted to a pH value of 9 with sodium hydroxide solution, and the undissolved polymer product separated. After the acidification of the salt solution with concentrated hydrochloric acid to pH 1, the product was separated by filtration and vacuum dried.

Yield of AHP was 63 g, 49% of theoretical yield.

EXAMPLE 5—Preparation of AHP

Into a stirred mixture of caprolactam (113 g, 1.0m), triethylamine hydrochloride (138 g, 1.0m) and water (60 g, 3.36m) was added phosphorus trichloride (292 g, 2.12m) over 40 minutes and at a temperature below 40° C. The reaction mixture was then heated over 120 minutes to 80° C. and held at this temperature for a further 240 minutes. During the total reaction time the reaction mixture was stirrable and no foaming took place. The reaction mixture was added to 400 ml of 20% hydrochloric acid (which was preheated to 60° C.) then heated to reflux and held for 120 minutes. Ming this process the pale orange product precipitated and was isolated by filtration. For further purification, the crude product was suspended in water, adjusted to a pH value of 9 with sodium hydroxide solution, and the undissolved polymer product separated. After the acidification of the salt solution with concentrated hydrochloric acid to pH 1, the product was separated by filtration and vacuum dried.

Yield of AHP was 162 g, 63% of theoretical yield.

EXAMPLE 6—Preparation of azacyclononane-2,2-diphosphonic acid

Into a stirred mixture of 2-azacyclononanone (30 g, 0.213M), triethylamine hydrochloride (29.2 g, 0.212M) and water (12.6 g, 0.7M), was added phosphorous trichloride (61.8 g, 0.213M) dropwise, with the addition rate adjusted to maintain the reaction mixture below 40° C. The reaction mixture was then heated over 60 minutes to 80° C. and held at this temperature for a further 150 minutes. During the total reaction time the reaction mixture was stirrable, becoming orange and opaque in appearance, although remaining homogeneous. The reaction mixture was then hydrolysed at approximately 70° C. by slowly adding water (200 ml), then heated to reflux and held at 85° C. for 60 minutes. The reaction mixture was then cooled to room temperature during which the reaction product crystallised out of the mixture, and was then isolated by filtration. To further purify the crude product it was firstly washed with water (approximately 200 ml) followed by washing with acetone (approximately 200 ml). Finally the product was vacuum dried.

The product was an off white/orange solid, identified by $^{31}P$ and $^{13}C$ NMR spectroscopy as azacyclononane-2,2-diphosphonic acid.

Yield of azacyclononane-2,2-diphosphonic acid was 28 g, 46% of theoretical yield.

EXAMPLE 7—Preparation of AHP

Into a stirred mixture of phosphorous acid flake (108.5 kg) and concentrated hydrochloric acid (245 kg, 36% w/w) was addded triethylamine (225 kg) over 2 hours. Caprolactam (287 kg) was then added, with phosphorous trichloride (702 kg) added over a 9½ hour period, with the addition rate adjusted to maintain the reaction mixture below 65° C. When the reaction was complete, the reaction mixture was then held at 53°–57° C. for 1 hour, and was then heated over 1½ hours to 85° C. and held at this temperature for a further 7.3 hours. During the total reaction time the reaction mixture was stirrable, with an orange mixture formed at the end of the reaction time. The reaction mixture was then hydrolysed by the addition over 40 minutes of the reaction mixture to water (900 kg). The crude product was an orange solid which was then isolated by filtration, slurried with water, adjusted with sodium hydroxide to pH 9.3 and then filtered. The filtrate was reacidified with concentrated hydrochloride acid to pH 0.9. A white solid was precipitated during this acidification stage. To further purify the product it was filtered, washed with water and vacuum dried.

Yield of azacycloheptane-2,2-diphosphonic acid was 442 kg, 45% of theoretical yield.

We claim:

1. A method for the production of an azacyclo diphosphonic acid, said acid being of the formula:

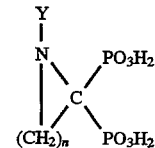

wherein n is a whole number of from 2 to 16 and Y is selected from the group consisting of H, unsubstituted alkyls, alkenyls, substituted alkyls, and aryls, said Y remains unchanged during the production of said acid, wherein said method comprises the following steps:

(a) reacting a mixture consisting essentially of (i) a lactam, (ii) a phosphorus trihalide, (iii) phosphorous acid and/or water, and (iv) at least one organic amine material selected from the group consisting of an organic amine and an organic amine salt, (b) hydrolysing said mixture, and (c) purifying the resultant product of step (b) to obtain said diphosphonic acid.

2. The method of claim 1, wherein n is a whole number of from 3 to 9.

3. The method of claim 1, wherein said lactam is selected from the group consisting of caprolactam and 2-azacyclononanone.

4. The method of claim 1, wherein said phosphorus trihalide is selected from the group consisting of phosphorus trichloride and phosphorus tribromide.

5. The method of claim 1, wherein said organic amine material is an organic amine which is a tertiary amine, selected from the group consisting of triethylamine and tributylamine.

6. The method of claim 1, wherein said organic amine material is an organic amine salt which is selected from the group consisting of organic amine hydrochloride, organic amine hydrobromide and an organic amine phosphorous acid salt.

7. The method of claim 6, wherein said organic amine material is an organic amine salt which is selected from the group consisting of a tertiary amine hydrochloride, a tertiary amine hydrobromide and a tertiary amine phosphorous acid salt.

8. The method of claim 7, wherein said organic amine salt is selected from the group consisting of triethylamine hydrochloride, triethylamine hydrobromide, a triethylamine phosphorous acid salt, tributylamine hydrochloride, tributylamine hydrobromide and a tributylamine phosphorous acid salt.

9. The method of claim 1, wherein said organic amine or said organic amine salt is present in said mixture in a ratio of from 0.1:1 to 4:1 molar, relative to said lactam.

10. The method of claim 9, wherein said ratio is 0.1:1 to 2:1 molar.

11. The method of claim 9, wherein said ratio is 0.5:1 to 2:1 molar.

12. The method of claim 9, wherein said ratio is about 1:1 molar.

13. The method of claim 5, wherein said phosphorous trihalide is selected from the group consisting of phosphorous trichloride and phosphorous tribromide; said lactam is selected from the group consisting of caprolactam and 2-azacyclononanone; and said organic amine is present in said mixture in a molar ratio of 0.5:1 to 2:1, relative to said lactam.

14. The method of claim 8, wherein said phosphorous trihalide is selected from the group consisting of phosphorous trichloride and phosphorous tribromide; said lactam is selected from the group consisting of caprolactam and 2-azacyclononanone; and said organic amine salt is present in said mixture in a molar ratio of 0.5:1 to 2:1, relative to said lactam.

15. The method of claim 1, wherein the mixture consists essentially of caprolactam, phosphorous trichloride, triethylamine hydrochloride and water.

16. The method of claim 1, wherein the mixture consists essentially of caprolactam, tributylamine hydrochloride, phosphorous trichloride and water.

17. The method of claim 1, wherein the mixture consists essentially of 2-azacyclononanone, triethylamine hydrochloride, water and phosphorous trichloride.

* * * * *